United States Patent
Fenc

(10) Patent No.: US 6,992,302 B2
(45) Date of Patent: Jan. 31, 2006

(54) BEDDING SANITIZER

(76) Inventor: Jerry Fenc, 413 Guildwood Pkwy., West Hill, Ontario (CA), M1E 1R3

( * ) Notice: Subject to any disclaimer, the term of this patent is extended or adjusted under 35 U.S.C. 154(b) by 57 days.

(21) Appl. No.: 10/629,180

(22) Filed: Jul. 29, 2003

(65) Prior Publication Data

US 2005/0023483 A1 Feb. 3, 2005

(51) Int. Cl.
    *A61L 2/10*       (2006.01)

(52) U.S. Cl. .................................. 250/455.11; 422/24

(58) Field of Classification Search ............. 250/455.11, 250/454.11; 422/24, 28, 29, 32, 121, 122
    See application file for complete search history.

(56) References Cited

U.S. PATENT DOCUMENTS

| | | | |
|---|---|---|---|
| 3,877,152 A | | 4/1975 | Gorman |
| 4,182,050 A | * | 1/1980 | Righi .......................... 34/60 |
| 4,562,869 A | | 1/1986 | Blum |
| 5,144,146 A | | 9/1992 | Wekhof |
| 5,252,190 A | * | 10/1993 | Sekiguchi et al. ........ 204/157.3 |
| 5,337,581 A | * | 8/1994 | Lott ............................. 62/264 |
| 5,546,678 A | * | 8/1996 | Dhaemers .................... 34/275 |
| 5,713,137 A | | 2/1998 | Fujita |
| 6,052,846 A | | 4/2000 | Patel et al. |
| 6,576,190 B1 | | 6/2003 | Park |
| 6,811,748 B2 | * | 11/2004 | Ettlinger et al. .............. 422/24 |

FOREIGN PATENT DOCUMENTS

| | | |
|---|---|---|
| CA | 2332669 | 7/2002 |
| CA | 2335398 | 7/2002 |
| CA | 2387280 | 11/2002 |
| CA | 2385170 | 6/2003 |
| EP | 0 356 896 | 7/1990 |
| JP | 02005999 A * | 6/1988 |

* cited by examiner

*Primary Examiner*—Kiet T. Nguyen
(74) *Attorney, Agent, or Firm*—Senniger Powers

(57) ABSTRACT

A sanitizer for bedding has an irradiation chamber with a light support mounted for reciprocation within the chamber. A light for radiating into the chamber is supported by said light support. A bedding support is mounted so as to be at least partially withdrawable from the chamber. The light support may be mounted medially within said chamber and the bedding support may extend on either side of the light support.

16 Claims, 7 Drawing Sheets

BEDDING SANITIZER

BACKGROUND

This invention relates to a sanitizer for bedding.

After a guest of a hotel leaves, the linens (comprising the bed sheets and pillow slips) on the bed occupied by the guest are removed and replaced with freshly laundered linens in preparation for receiving the next guest. On the other hand, the heavier bedding—the pillows, blankets, and bedspreads—is normally cleaned only infrequently, typically by being sent out for drycleaning.

This same approach is used in hospitals, with linens of a bed being changed between patients, and heavier bedding being cleaned only infrequently, typically by drycleaning.

A drawback with this approach is that it compromises on the cleanliness of the bedding.

SUMMARY OF THE INVENTION

A user of a bed, particularly if ill, may impart germs not only to the linens, but also to the heavier bedding. In such a situation, if the heavier bedding is not cleaned between users, there is a risk that the next user of the bed may be exposed to these germs and possibly contract an illness.

Recognizing this problem, the present invention provides a sanitizer for bedding that has an irradiation chamber with a light support mounted for reciprocation within or adjacent the chamber and a light for radiating into the chamber supported by the light support.

In one aspect, a bedding support is mounted so as to be at least partially withdrawable from the chamber. In another aspect, the light is a narrow spectrum light. In a further aspect, there are a plurality of light supports mounted for reciprocation within or adjacent the chamber with each of the plurality of light supports supporting a light for radiating into the chamber.

Other features and advantages of the invention will become apparent from a review of the following description in conjunction with the drawings.

BRIEF DESCRIPTION OF THE DRAWINGS

In the figures which illustrate example embodiments of the invention.

DETAILED DESCRIPTION

The present invention contemplates a method of operating a facility having beds. Such a facility could be a hotel, a hospital, or even an airplane where the seats of the plane act as beds for travellers. The method involves removing used bedding from a bed of the facility after departure of a user. The used bedding, or other bedding, is sanitized by irradiating the bedding with narrow spectrum radiation, such as ultraviolet ("UV") radiation. To provide more thorough sanitization, during the irradiation air may be circulated about the bedding. The bed is made up with the sanitized bedding.

This approach is particularly suited to heavier bedding, such as blankets, pillows, and bedspreads, which is not amenable to regular laundering. So that the method may best ensure a healthy environment, used bedding may be replaced with sanitized bedding every time a new user of the bed departs.

Where the bedding comprises a blanket or a bedspread, sanitization may be facilitated by moving a narrow band radiation source (for example an ultraviolet light) along opposite sides of the blanket or bedspread at a stand-off from the blanket or bedspread. This may be accomplished by draping the blanket or bedspread over a support prior to exposing the bedding to narrow band radiation.

Where the facility is a multi-floor building, such as a hotel or hospital, it may be more cost effective to implement the method with one or more portable sanitizers that may be deployed on each floor to receive and sanitize used bedding as it is removed from each bed. Bedding, once sanitized, may then be returned to the bed from which it was removed, or find its way onto another bed.

A suitable sanitizer to effect the described method for blankets and bedspreads, such as duvets, is shown in the figures.

Figure 1:
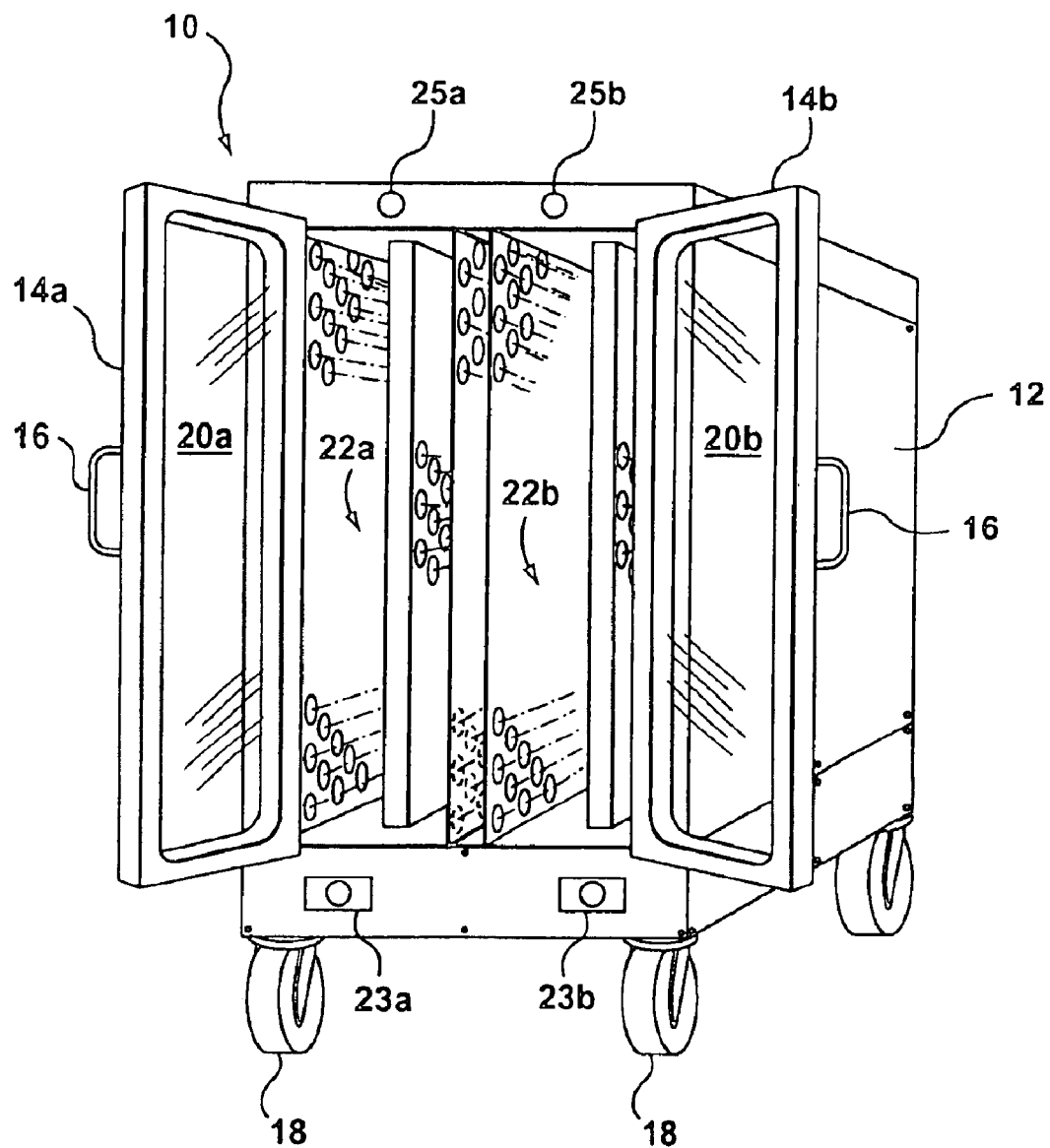
FIG. 1 is a perspective view of a sanitizer made in accordance with this invention.
Figure 2:
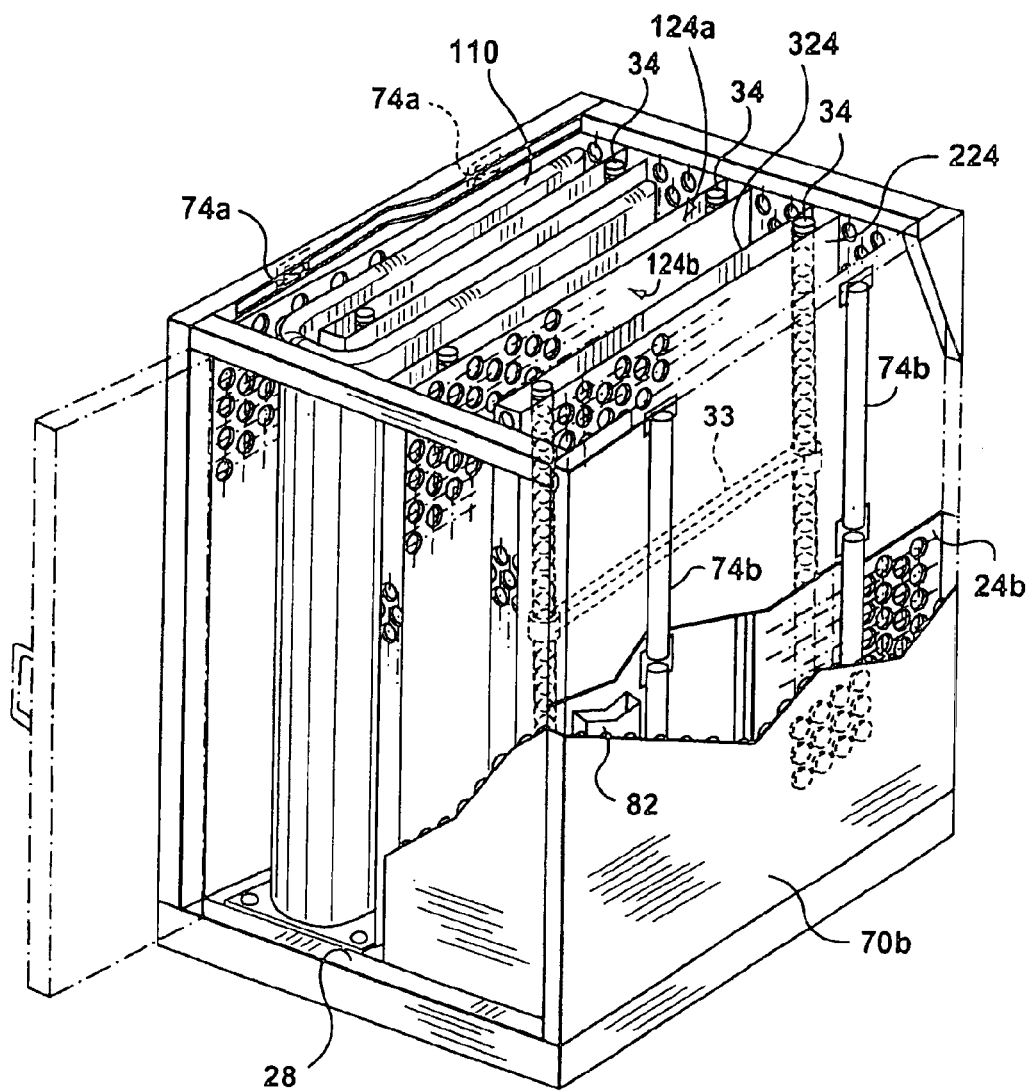
FIG. 2 is a partially broken away perspective view of the sanitizer of FIG. 1.
Figure 3:
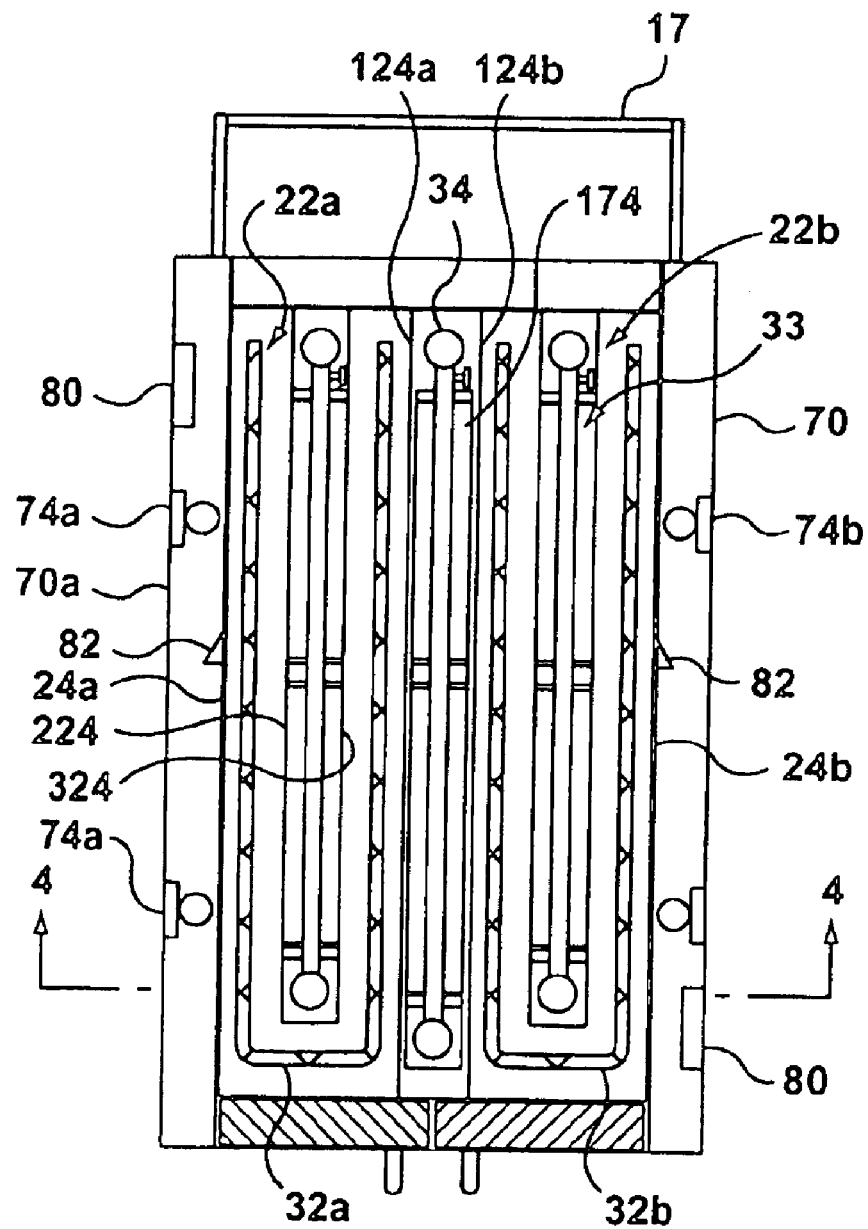
FIG. 3 is a cross-sectional view along the lines 4—4 of FIG. 4.
Figure 4:
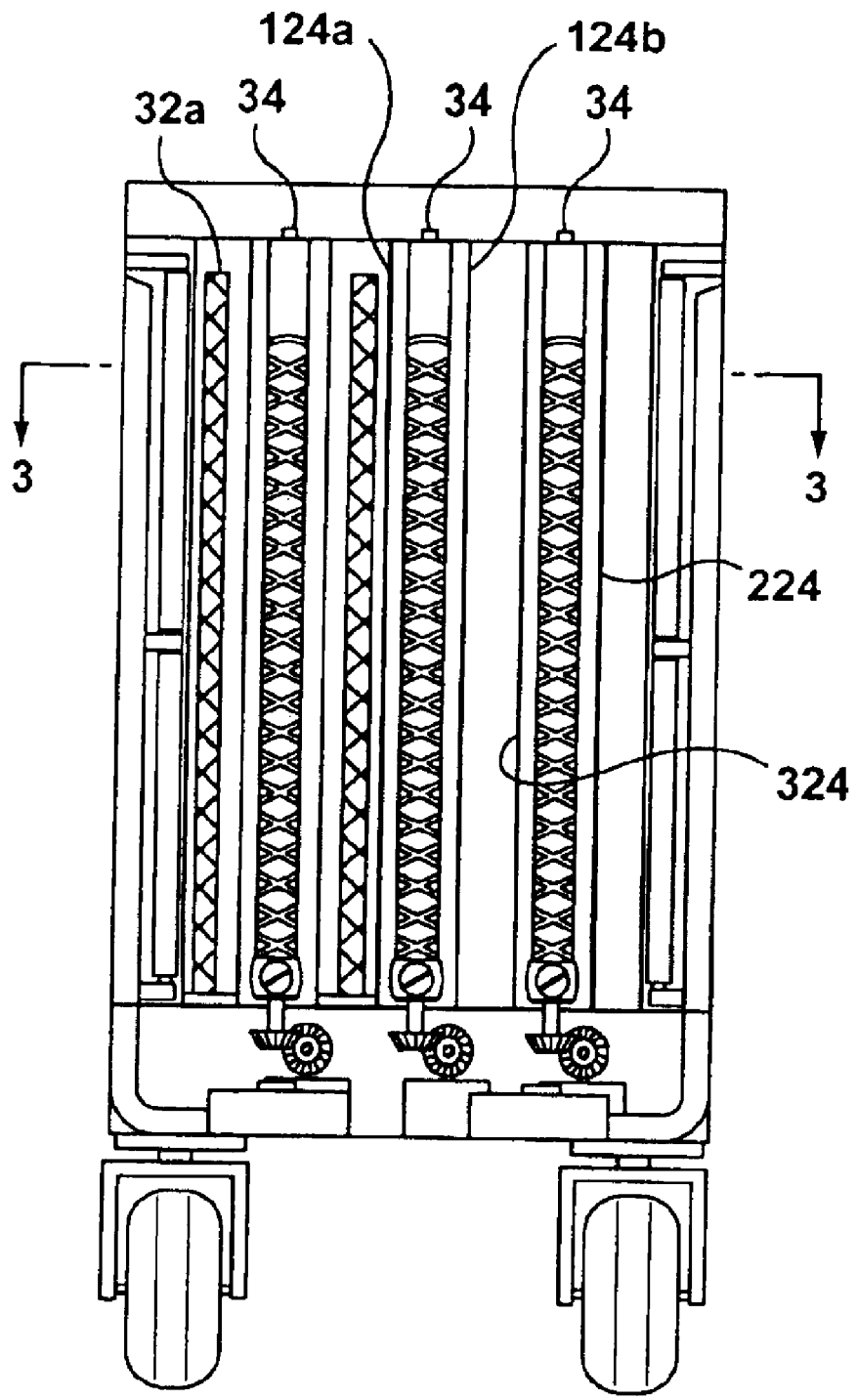
FIG. 4 is a cross-sectional view along the lines 3—3 of FIG. 3.
Figure 5:
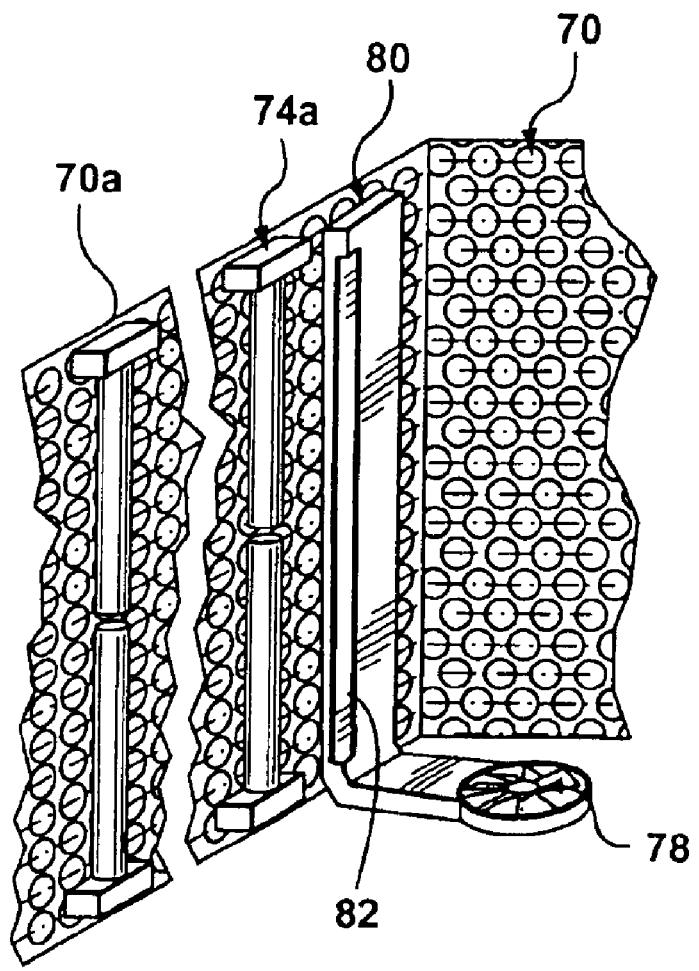
FIG. 5 is a perspective break out view of a portion of the sanitizer of FIG. 1.

Turning to FIG. 1, a sanitizer 10 has a cabinet 12 with a pair of outwardly opening access doors 14a, 14b. Each door may be provided with a UV opaque window 20a, 20b to allow viewing of irradiation chambers 22a, 22b, respectively, inside cabinet 12. The doors may have a latch (not shown) and opening handles 16. The cabinet may be provided with a handle 17 (FIG. 3) and wheels 18 to make the sanitizer 10 portable. A pair of butterfly valves 23a, 23b and a pair of vents 25a, 25b allow ambient air to be admitted into cabinet 12 when the ambient air pressure exceeds that inside the cabinet.

Referencing FIGS. 2 to 5 along with FIG. 1, irradiation chamber 22a is defined by a pair of perforated walls 24a and 124a supported on the floor 28 of cabinet 12. Irradiation chamber 22b is similarly configured with perforated walls 24b and 124b.

The inner face of the walls 70 of cabinet 12 is high gloss and embossed. Walls 70 may be fabricated of aluminum. A first pair of fixed, vertically directed UV lights 74a extends between a side wall 70a of cabinet 12 and adjacent wall 24a of irradiation chamber 22a. A further pair of UV lights 74b extends between a side wall 70b of cabinet 12 and adjacent wall 24b of chamber 22b. The UV lights emit narrow spectrum radiation at a germicidal wavelength, e.g., 2,537 Angstroms.

A fan 78 extends through floor 28 of cabinet 12 and forces air into a chimney 80 and through a side opening 82 of the chimney into the gap between the cabinet wall 70a and wall 24a. Air deflectors 84 in wall 24a deflect air flowing in the space between the cabinet wall 70a and wall 24a into the irradiation chamber 22a. Irradiation chamber 22b is similarly configured.

Wall 124a of irradiation chamber 22a and wall 124b of irradiation chamber 22b form a gap therebetween which accommodates horizontally directed UV lights 174 that are mounted to a carriage 33 which is supported between two screws 34. Additionally, each irradiation chamber is bi-sected by a pair of perforated walls 224 and 324 forming a gap therebetween which receives horizontally directed UV lights 174 that are mounted to a carriage 33 supported between two screws 34.

The perforated walls 24a, 24b, 124a, 124b, 224, and 324 may be made of stainless steel.

Each irradiation chamber 22a, 22b has a slidable U-shaped bedding support 32a, 32b which may be slid outwardly when the doors 14a, 14b are open. When fully inserted into an irradiation chamber, each bedding support surrounds the pair of perforated walls 224, 324 bisecting the chamber. Each bedding support is formed as a mesh with large openings to pass air and light. (Note that FIG. 1 is shown with the bedding supports removed and FIG. 2 with one support removed.)

Figure 6:
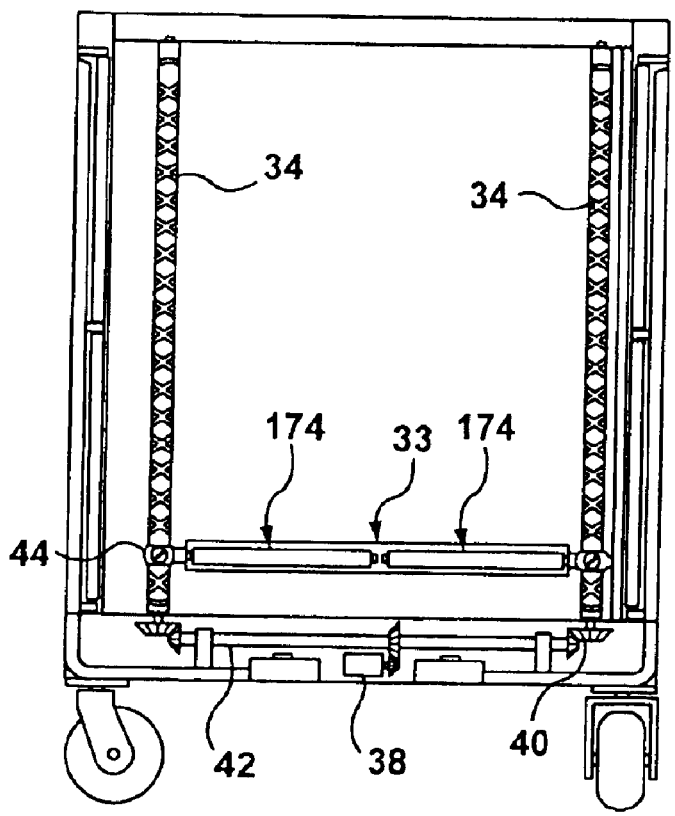
FIG. 6 is a schematic side view of a portion of the sanitizer of FIG. 1.
Figure 7:
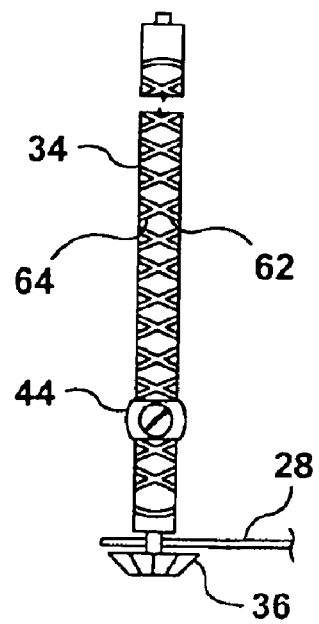
FIG. 7 is a schematic side view of a portion of the sanitizer of FIG. 1.

The screws 34 are threaded along their length and may be made of carbon steel alloy C-1045 which does not require lubrication. With reference to FIGS. 6 and 7, each screw 34 extends through floor 28 and terminates in a bevel gear 36. Each bevel gear is driven by a motor 38 through a series of bevel gears 40 and shafts 42.

Figure 8:
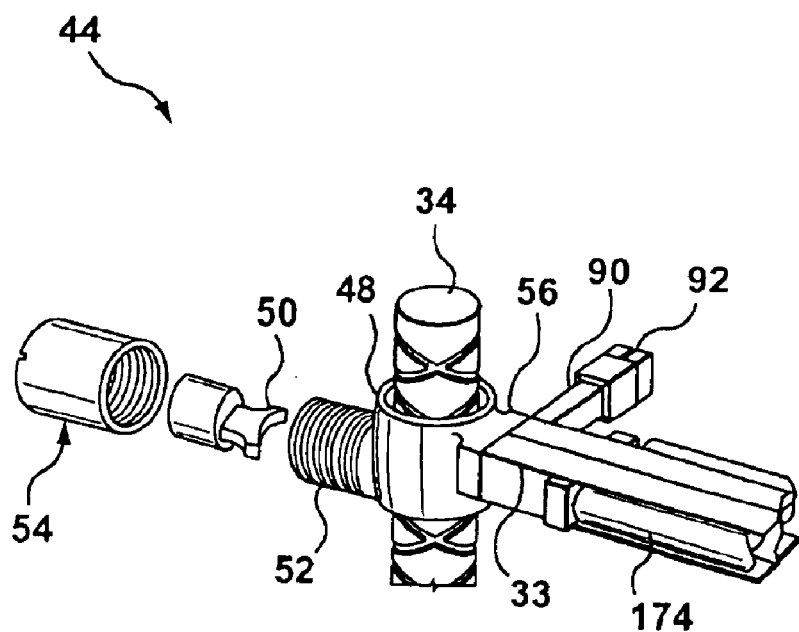
FIG. 8 is an exploded perspective view of a portion of the sanitizer of FIG. 1.

Each of the six screws is threaded with a first spiral thread 62 and a second spiral thread 64 arranged to form a "figure-8" pattern along the screw. The first and second spiral threads 62, 64 meet at the top end of the screw 34 and at the base of the screw.

Figure 9:
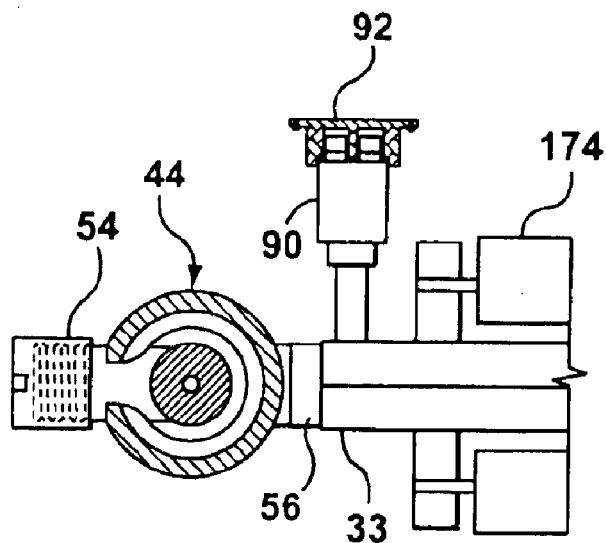
FIG. 9 is a schematic top view of a portion of the sanitizer of FIG. 1.

Turning to FIG. 8, An annulus 48 of a lifting assembly 44 surrounds each screw 34 and a tooth 50 fitted into a tube 52 extending from annulus 48 engages the threads of a screw 34. A cap 54 threaded onto the tube 52 retains the tooth 50 in position. An inwardly directed flange 56 extends from annulus 48 and into a receptor in carriage 33. With reference to FIG. 9, power may be transferred to lights 174 through a connector 90 which slides along a power bar 92.

Sanitizer 10 is suited for use in sanitizing bedding, such as bedspreads and blankets. More specifically, doors 14a, 14b may be opened and each bedding support 32a, 32b slid outwardly. A bedspread or blanket 110 (FIG. 2) may then be draped over each support, the supports re-inserted into the irradiation chambers, and the doors closed. Thereafter, UV lights 74a, 74b, 174 may be illuminated and motors 38 and fans 78 activated. With the motors activated, the shaft and bevel gear arrangement rotates bevel gears 36 and, therefore, each of screws 34 in the same rotational direction. This rotational direction is such that as a screw 34 rotates, its lifting assembly 44 moves upwardly along the first spiral screw thread 62. Thus, the lifting assemblies of each of the six screws act to lift the UV lights 174.

Once the lifting assemblies reach the upper end of the screws 34, continued rotation of the motors causes the tooth of each lifting assembly to track the second spiral screw thread 64 of the screw 34. In consequence, the lifting assemblies now move downwardly so that the lifting assemblies act to lower the UV lights 174 until the lights return to their lowermost position. At this point, the tooth of each lifting assembly begins again to track the first spiral screw thread 62 of the screw 34. As a result, the UV lights 174 repeatedly reciprocate as the motors continue to rotate. The reciprocation of UV lights 174 exposes the entire adjacent face of the blanket/bedspread to the UV light while assisting in assuring that the bedding inside the sanitizer does not overheat.

It will be apparent that with this arrangement, the UV lights 174 may be reciprocated by simply rotating the motors in one rotational direction. Of course, a less elegant alternative would be to replace the screws with ball screws and control the motors to switch rotational direction at each end of the stroke of the bedding supports.

In contrast to UV lights 174, UV lights 74a, 74b are fixed. However, the circulated air assists in ensuring the bedding inside the sanitizer does not overheat.

During sanitization, fans 78 circulate air in the irradiation chambers 22a, 22b. The embossments of the inner surface of the walls 70 of cabinet 12 reflect the UV light in all directions and impart turbulence to the circulating air. This turbulent air acts to dislodge loose particles on or in the bedding. Throughout, the UV lights emit UV radiation into the irradiation chambers which acts to neutralize germs (e.g., bacteria) exposed to the light.

The sanitation of the bedding in the sanitizer 10 may continue for a period of time in order to sufficiently sanitize the bedding. Thereafter, the UV lights may be extinguished and the motors and fans de-activate so that the doors 14a, 14b may be opened and the sanitized bedding removed.

The sanitizer may have a control panel (not shown) used to control parameters of the sanitizer such as the period of sanitization.

As an alternative to using UV light, far-infrared radiation may be used to sanitize the bedding in the sanitizer. In such instance, the bedding should be first wetted with a small amount of water. This technique is further described in U.S. publication number 2002 00 95946 published Jul. 4, 2002, the contents of which are incorporated by reference herein. A drawback with this approach is that is may take considerable time to dry the bedding.

Other modifications will be apparent to those skilled in the art and, therefore, the invention is defined in the claims.

What is claimed is:

1. A sanitizer for bedding comprising:

an irradiation chamber;

a light support mounted for reciprocation within said chamber;

a light for radiating into said chamber, said light supported by said light support; and a bedding support mounted so as to be at least partially withdrawable from said chamber.

2. The sanitizer of claim 1 wherein said light support is mounted medially within said chamber.

3. The sanitizer of claim 2 wherein said bedding support supports bedding such that it extends on either side of said light support.

4. The sanitizer of claim 1 further comprising a motor for reciprocating said light support.

5. The sanitizer of claim 1 further comprising:

a second light support mounted for reciprocation adjacent said chamber; and a second light for radiating into said chamber, said second light supported by said second light support.

6. The sanitizer of claim 1 wherein said light is a narrow spectrum light.

7. The sanitizer of claim 1 wherein said light is an ultraviolet light.

8. The sanitizer of claim 1 further comprising a fan for circulating air within said irradiation chamber.

9. The sanitizer of claim 8 wherein walls of said chamber are embossed to impart turbulence to air circulated in said chamber.

10. The sanitizer of claim 1 wherein said light support comprises screws.

11. The sanitizer of claim 10 wherein each of said screws is threaded with a first spiral thread and a second spiral thread, said first spiral thread meeting said second spiral thread at a top end of said screw, said first spiral thread and second spiral thread arranged such that a direction of tracing that traces said first spiral thread toward said top end of said screw traces said second spiral thread away from said top end of said screw.

12. The sanitizer of claim 11 further comprising at least one motor for driving said screws in said direction.

13. The sanitizer of claim 12 wherein said light support comprises a lifting assembly surrounding each of said screws, each lifting assembly supported by a thread of said screw so that rotation of said screws in said direction causes said lifting assemblies to trace one of said first spiral thread and said second spiral thread.

14. A sanitizer for bedding comprising:

an irradiation chamber;

a plurality of light supports mounted for reciprocation within or adjacent said chamber;

each of said plurality of light supports supporting a light for radiating into said chamber.

15. The sanitizer of claim 14 further comprising:

a bedding support mounted so as to be at least partially withdrawable from said chamber.

16. A sanitizer for bedding, comprising:

an irradiation chamber;

a support mounted for reciprocation within said chamber; and a narrow spectrum light for emitting into said chamber, said light supported by said support for reciprocation.

* * * * *